United States Patent
Bruder et al.

(10) Patent No.: US 7,039,152 B2
(45) Date of Patent: May 2, 2006

(54) METHOD FOR PRODUCTION OF TOMOGRAPHIC SECTION IMAGES OF A PERIODICALLY MOVING OBJECT WITH A NUMBER OF FOCUS DETECTOR COMBINATIONS

(75) Inventors: Herbert Bruder, Hoechstadt (DE); Thomas Flohr, Uehlfeld (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/991,454

(22) Filed: Nov. 19, 2004

(65) Prior Publication Data
US 2005/0111622 A1  May 26, 2005

(30) Foreign Application Priority Data
Nov. 20, 2003 (DE) ............... 103 54 214

(51) Int. Cl.
*A61B 6/00* (2006.01)

(52) U.S. Cl. .................. 378/8; 378/62; 378/901; 600/428

(58) Field of Classification Search .......... 378/4, 378/8, 15, 19, 62, 85, 901; 600/425, 428
See application file for complete search history.

(56) References Cited

U.S. PATENT DOCUMENTS

| | | | |
|---|---|---|---|
| 4,196,352 A | 4/1980 | Berninger et al. ........... 378/7 |
| 4,384,359 A | 5/1983 | Franke ......................... 378/9 |
| 4,991,190 A | 2/1991 | Mori ............................ 378/9 |
| 5,966,422 A | 10/1999 | Dafni et al. ................. 378/9 |
| 6,041,097 A | 3/2000 | Roos et al. ................. 378/62 |
| 6,421,412 B1 | 7/2002 | Hsieh et al. ................. 378/9 |
| 6,445,761 B1 | 9/2002 | Miyazaki et al. ............ 378/8 |

(Continued)

FOREIGN PATENT DOCUMENTS

DE      198 42 238 A1      4/2000

(Continued)

OTHER PUBLICATIONS

H. Bruder et al., "A Novel Reconstruction Scheme for Cardiac Volume Imaging With MSCT Providing Cone Correction", Medical Imaging 2002, pp. 60-73.

(Continued)

*Primary Examiner*—David V. Bruce
*Assistant Examiner*—Courtney Thomas
(74) *Attorney, Agent, or Firm*—Harness, Dickey & Pierce P.L.C.

(57) ABSTRACT

A method and CT scanner are proposed for the production of tomographic section images, in particular X-ray CT images, of a periodically moving object with periodically changing movement and rest phases. For scanning, a number of focus detector combinations with flat detectors are moved on coaxial spiral paths and movement signals from the moving object are measured at the same time in order to detect movement and rest phases. Further, the time correlation between the movement data and the detector output data stored and axial segment image stacks are then reconstructed independently of one another from sub-segments of the spiral paths using the detector output data from each detector which represent a rest phase of the moving object. Additionally, segment image stacks from the n spiral paths of the n focus detector combinations at the correct time are added up in a complementary angle form and in layers to form 180° tomography section images. The axial segment image stacks are reconstructed in a first step from double-inclined reconstruction planes. Further, in a second step, they are reformatted to produce axial segment image stacks, and detector data from a number of successive movement periods are used for this purpose.

25 Claims, 6 Drawing Sheets

U.S. PATENT DOCUMENTS

| | | | |
|---|---|---|---|
| 6,504,893 B1 | 1/2003 | Flohr et al. | 378/8 |
| 6,658,081 B1 | 12/2003 | Bruder et al. | 378/15 |
| 6,665,370 B1 | 12/2003 | Bruder et al. | 378/15 |
| 6,937,690 B1 * | 8/2005 | Bruder et al. | 378/15 |
| 2004/0114708 A1 | 6/2004 | Bruder et al. | 378/4 |
| 2005/0111623 A1 * | 5/2005 | Bruder et al. | 378/95 |

FOREIGN PATENT DOCUMENTS

| | | |
|---|---|---|
| DE | 199 57 082 A1 | 8/2001 |
| DE | 101 27 269 A1 | 1/2003 |
| DE | 101 33 237 A1 | 5/2003 |
| DE | 102 44 180 A1 | 4/2004 |
| DE | 103 02 565 A1 | 8/2004 |

OTHER PUBLICATIONS

Thomas Flohr et al., "Heart Rate Adaptive Optimization of Spatial and Temporal Resolution for Electrocardiogram-Gated Multislice Spiral CT of the Heart", Journal of Computer Assisted Tomography, vol. 25, No. 6, pp. 907-923.

Karl Stierstorfer et al., "Segmented multiple plane reconstruction: a novel approximate reconstruction scheme for multi-slice spiral CT", Physics in Medicine and Biology 47 (2002), pp. 2571-2581.

* cited by examiner

METHOD FOR PRODUCTION OF TOMOGRAPHIC SECTION IMAGES OF A PERIODICALLY MOVING OBJECT WITH A NUMBER OF FOCUS DETECTOR COMBINATIONS

This application claims priority on German application No. DE 10354214.0 filed on Nov. 20, 2003, the entire contents of which are hereby incorporated herein by reference.

FIELD OF THE INVENTION

The invention generally relates to a method for production of tomographic section images, in particular X-ray CT images, of a periodically moving object with periodically changing movement and rest phases. A number of focus detector combinations are moved around the examination object on coaxially running paths with the same pitch in order to scan the periodically moving examination object. Further, movement signals from the examination object at the same time are measured in order to determine movement and rest phases, and are stored correlated with the detector output signals.

BACKGROUND OF THE INVENTION

Computer tomography methods for creation of section images with the aid of multiple focus detector combinations are known, for example, from the patent specifications U.S. Pat. No. 4,196,352, U.S. Pat. No. 4,384,359, U.S. Pat. No. 5,966,422, U.S. Pat. No. 4,991,190 and U.S. Pat. No. 6,421,412 B1. The Laid-Open Specification DE 199 57 082 discloses the recording of movement signals of the heart by use of an EKG in order to display a beating heart in parallel with the scanning process, in order that the rest phases of the heart can be determined and in order that exclusively images from the rest phase can be assessed, with the X-ray source additionally being active only during the rest phase in the cited document.

However, the documents cited above in principle make use of spiral reconstruction methods which are based on a complete 180° spiral data record. This means that a large amount of measurement information cannot be used since only measurement data at the correct time. That is to say, data measured in the same heart phase, can be used. This data jointly results in a 180° spiral data record.

The Laid-Open Specification DE 10 127 269 A1 discloses how segment images are created from incomplete spiral data records which intrinsically include only a portion of a 180° segment of a spiral scan. These segment images then lead to complete CT scan images by addition of a number of segment images in a segment stack. Laid-Open Specification DE 10 133 237 A1 also discloses the application of the abovementioned SMPR (Segmented Multiple Plane Reconstruction) method for the display of periodically moving objects, although the cited document describes only a solution for a CT scanner with a single revolving focus. Another similar method is the ACMPR (Adaptive Cardio Multiple Plane Reconstruction) method, which is a generalization of the SMPR method with the segment length additionally being variable.

With regard to the SMPR method, reference should be made to the document by Stierstorfer, Flohr, Bruder: *Segmented Multiple Plane Reconstruction: A Novel Approximate Reconstruction Scheme for Multislice Spiral CT.*, Physics in Medicine and Biology, Vol. 47 (2002), pp. 2571–2581. With regard to this ACMPR method, reference should be made to the literature reference T. Flohr, B. Ohnesorge, 'Heart-Rate Adaptive Optimization of Spatial and Temporal Resolution for ECG-Gated Multislice Spiral CT of the Heart', JCAT vol. 25, No. 6, 2001, and to H. Bruder et al., 'A Novel Reconstruction Scheme for Cardiac Volume Imaging with MSCT Providing Cone Correction', Medical Imaging 2002, Image Processing, Vol 4684, pp. 60–72. The disclosure content of both documents is hereby incorporated herein by reference, in their entirety.

The problem of these known and so-called SMPR—or ACMPR—methods is that the time resolution that is achieved when scanning a periodically moving heart is not sufficient to achieve sufficiently sharp image representations.

SUMMARY OF THE INVENTION

An object of an embodiment of the invention is therefore to provide a method for production of tomographic section images of periodically moving examination objects, which makes it possible to achieve better time resolution. At the same time, a further aim of an embodiment of the invention is to propose a CT scanner which is suitable for this purpose.

The inventors have discovered that it is possible, when using the cardio-SMPR method, which is known per se, in which a large number of incomplete segment images (which are obtained by reconstruction from spiral segments over an angle range of less than 180°) and subsequent superimposition of the incomplete segment images of a segment stack are used to produce a CT scan, to create images with high time resolution of a moving examination object when the simultaneously measured data from a number of focus detector combinations from a number of rest phases of adjacent movement cycles of the periodically moving examination object is used to produce a segment stack. However, when forming the segment images, care should be taken to ensure that the sum of the segment images in total is composed of segments which correspond to a 180° scan.

On the basis of these fundamental statements, the inventors propose a method for production of tomographic section images, in particular X-ray CT images, of a periodically moving object with periodically changing movement and rest phases, preferably of a heart of a living being, preferably of a patient, comprising:

in order to scan the at least partially periodically moving object, n focus detector combinations with flat detectors, preferably multiple line detectors, are moved on n coaxial spiral paths relative to the object to be examined, with detector output data from the multiple line detectors, which represent the attenuation of beams which originate from the focus as they pass through the examination object, being gathered together with the indirect or direct spatial orientation data of the beams, at the same time, movement signals, preferably EKG signals, of the moving object are measured for detection of movement and rest phases, with the time correlation between the movement data and the detector output data being stored, axial segment image stacks are then reconstructed independently of one another from sub-segments of the spiral paths using the detector output data from each detector which represent a rest phase of the moving object, and segment image stacks from the n spiral paths of the n focus detector combinations at the correct time are added up in a complementary angle form and in layers to form 180° tomography section images, with the axial segment image stacks being reconstructed in a first step from double-inclined reconstruction planes and, in a second step, being reformatted to produce axial segment image stacks, in order to take into account a conical beam geometry, and detector data from a number of successive movement periods being used for this purpose.

The ACMPR method, which represents a generalization of the SMPR method with a variable segment length, is thus adapted for n focus detector combinations, with the ACMPR method for 180°/n segments being applied separately to each of the n 180°/n data angles. Complete 180° segments are therefore not used for the ACMPR method and, instead of this, importance is now placed during the image addition process on the sum of all the added-up images resulting in a data record which covers 180°.

According to an embodiment of the invention, a parallel rebinning process, preferably line by line parallel rebinning, is preferably carried out before the back-projections.

It is particularly advantageous and economic to use two and only two focus detector combinations, whose angles are offset with respect to one another and which are preferably arranged at right angles to one another, since this keeps the hardware complexity within limits while at the same time achieving major progress in the direction of better time resolution. Alternatively, it may also be conditionally economic to use three and only three focus detector combinations, whose angles are offset with respect to one another and which are preferably offset through 180°/3, although, in this case, the improvement which is achieved in the time resolution is scarcely related to the costs involved.

Particularly when using two focus detector combinations, it is advantageous to use at least one focus detector combination whose aperture angle is greater, preferably considerably greater, than the aperture angle of the at least one other focus detector combination. In the case of three focus detector combinations, this is very difficult purely for geometric reasons, but is possible in principle.

Advantageously, in the case of a refinement such as this, the aperture angle that is used, preferably also the active area of the corresponding beam, of the larger focus detector combination can be restricted before the scanning process such that it is identical to the aperture angles of the other focus detector combination.

Furthermore, it corresponds to a preferred embodiment when each focus detector combination runs on a dedicated spiral path, which is offset with respect to the spiral paths of the other focus detector combinations. This is necessarily the case, for example, when the focus detector combinations are arranged on one plane.

However, it is also possible to arrange at least two focus detector combinations offset with respect to one another in the z direction such that they run on a common coincident spiral path. For this type of arrangement, the offset of the at least two focus detector combinations in the z direction can also be set as a function of a selected spiral pitch, so that the spiral paths are always coincident irrespective of the selected forward movement.

A further advantageous embodiment of the method according to the invention may include the rotation rate being set on the basis of the period duration of the moving examination object, preferably on the basis of the movement frequency of the examined object, preferably of the heart, such that the best-possible time resolution is achieved when using a number of successive cycles for image reconstruction. For a two focus detector combination, and for the two-segment reconstruction which results from this, this means that the two spiral data segments which are acquired relating to adjacent cycles must be of the same length.

Furthermore, in order to reduce the dose load on the examination object, the radiation which originates from at least one focus can be controlled indirectly or directly over at least the majority of the movement phase, by which means measured movement signals can be switched off, or at least reduced.

One special embodiment of the method according to an embodiment of the invention may include the data from the focus detector combination with a small fan angle, which covers a relatively small section field, being used by data from the focus detector combination with a large fan angle, which covers a larger section field, to supplement the detector data from the larger detector.

In addition to the method described above, the inventors also propose an imaging CT scanner, in particular an X-ray CT scanner, which has at least the following features:
 two coaxially arranged focus detector combinations which can be moved in a spiral shape along a common rotation axis in order to scan a periodically moving object, relative to this object,
 a means for movement detection and in order to distinguish between rest and movement phases of the periodically moving object, preferably an EKG, and
 means, preferably program means, which are designed such that the method according to the invention outline above is carried out.

In the case of a CT scanner such as this, it is also advantageous for at least two focus detector combinations to use fan aperture angles of different size, in which case the magnitude of the fan aperture angle on at least one focus detector combination is preferably adjustable. The distance between the focus and the detector may also be different for two focus detector combinations.

BRIEF DESCRIPTION OF THE DRAWINGS

The invention will be described in more detail in the following text with the aid of the figures, with the following reference symbols and variables being used in this case: 1 CT scanner; 2 first tube; 3 first detector; 4 second tube; 5 second detector; 6 housing; 7 opening; 8 couch; 9 z-axis; 10 control/evaluation unit; 11 first beam; 12 second beam; 13 first/small section field; 14 second/large section field; 15 shutter for the second beam; 16 shutter for the first beam; 17 R spike/R peak in the EKG; 18 EKG line; 19 reconstructable volume element with data from one heart cycle; 20 reconstructable volume element with data from two heart cycles; 21 time return to the start of the rest phase; 22 detector lines; 23 virtual detector; 24 segment image stack; 25 intermediate image/segment image plane; $D_1$ first detector; $D_2$ second detector; k number of the half revolution of the gantry; $L_1$ length of the first detector; $L_2$ length of the second detector; P patient; $P_{rgn}$ n-th program module; p polar coordinate; $P_{n,max}$ maximum position of the detector n; $S_n$ n-th spiral data record; $SB_n$ spiral path of the n-th focus $F_n$; t time axis; $t_{njs}$ time position corresponding to $\alpha_{njs}$ (start position); $t_{nje}$ time position corresponding to $\alpha_{nje}$ (n position); $T_{rev}$ retrospective time offset of the next R spike in the EKG with respect to the start of the rest phase; $T_R$ time of the R spike; $T_{RR}$ duration of a heart cycle from one R spike to the next; $T_{rot}$ revolution time of the gantry; $USB_n$ sub-segment of the spiral path $SB_n$; $z_{img}$ z position of the image; α rotation angle of the gantry/projection angle; $\alpha_n$ start angle; $\alpha_{js}$ start projections of the segment elements; $\alpha_{je}$ end projections of the segment elements; $\alpha_{nms}$ m-th start angle of the n-th focus; $\beta_1$ fan angle of the first beam; $\beta_2$ fan angle of the second beam; $\Delta T_{ima}$ image time resolution; $\theta_n$ n-th segment element.

In the figures, in detail.

DETAILED DESCRIPTION OF THE EXEMPLARY EMBODIMENTS

Figure 1:
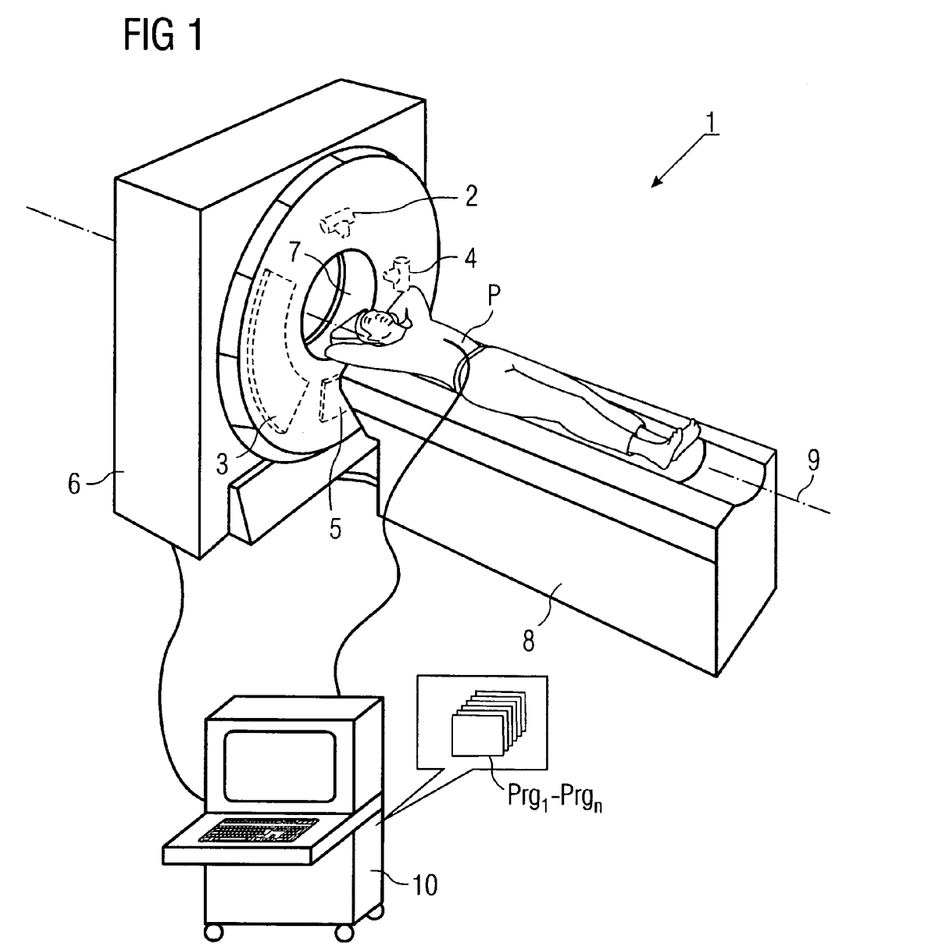
FIG. 1 shows a 3D illustration of a CT scanner with two focus detector combinations, including an evaluation unit with an integrated EKG.

FIG. 1 shows a 3D illustration of one preferred exemplary embodiment of a CT scanner 1 with two focus detector combinations 2, 3, and 4, 5, which are mounted on a gantry (which is not illustrated) within the housing 6 such that they can rotate. The illustration shows only X-ray tubes 2 and 4, however, since the actual focus is located within the tube. Controlled by the control and evaluation unit 10 and by the control and evaluation programs $Prg_n$ integrated in it, the patient P is moved along the z axis 9 with the aid of the movable patient couch 8 through the opening 7 in the CT scanner 1, while the gantry is at the same time rotated, with the two focus detector combinations 2, 3 and 4, 5, about the z axis 9. With respect to the patient as the reference system, this results in spiral movement paths of the foci. If the foci are arranged on one plane, then each focus runs on its own spiral path $SB_n$ (see FIG. 4), which is shifted with respect to the other spiral path corresponding to its angle offset in the direction of the z axis 6.

At the same time as the scanning of the patient P via the focus detector combinations, the movement signals of the heart are scanned via an EKG which is integrated in the control/evaluation unit 10, from which it is retrospectively possible to determine the rest phase prior to the respectively measured heart cycle on the basis of the R spike detected in the EKG.

Figure 2:
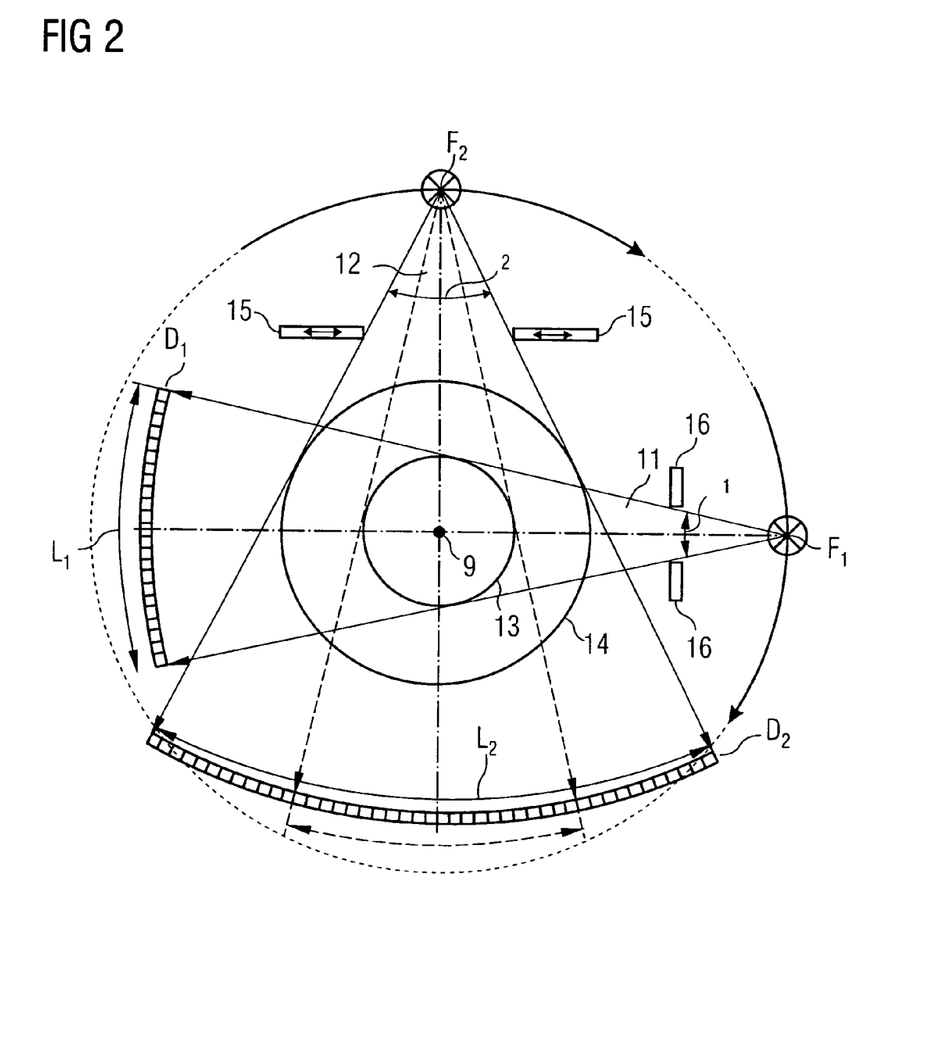
FIG. 2 shows a schematic illustration of a recording system with two focus detector combinations, respectively having a large and a small fan angle, and in each case offset through 90° with respect to one another.

In order to assist understanding, FIG. 2 shows the scanning system of the two focus detector combinations once again in the form of a schematic section illustration, although the X-ray tubes which form the respective foci $F_1$ and $F_2$ are not shown here. This illustration thus shows the two focus detector combinations from FIG. 1 respectively with a first focus $F_1$ and a second focus $F_2$, and the respective multiple line detectors $D_1$ and $D_2$ arranged opposite them. A beam 11 with a relatively small fan angle $B_1$, which is set in a fixed form by the shutter 16, passes from the focus F1 to the opposite detector $D_1$, which has a length $L_1$ in the direction of the fan angle $\beta_1$, and has a number of detector lines in the z direction. The second focus detector combination $F_2$, $D_2$ is arranged essentially at right angles to the imaginary connecting line between the focus $F_1$ and the detector $D_1$. These focus detector combinations $F_2$, $D_2$ have a variable, larger fan angle $\beta_2$, however, whose widening can be set on the one hand to the angle of the first beam fan $\beta_1$ or to a broader angle. The fan angle is in this case set by use of a movable shutter 15. If, exceptionally, both fan angles are set to be of the same magnitude, then only the area located in the small section field 13 is scanned, while the larger section field 14 can be scanned completely if the second beam 12 is set to be wider.

If the beams are set to have different widths, then the data for the smaller section field 13 from the smaller detector $D_1$ can and should be supplemented by data from the larger section field 14 from the larger detector $D_2$. This principle of data supplementation is illustrated in more detail in FIG. 3. This FIG. 3 uses a polar coordinate system z, p to show a virtual detector 23 which has the detector lines 22 from the detector $D_1$ centrally, and which is supplemented peripherally by the data from the detector lines 22 in the second detector $D_2$. However, since this detector information does not originate from the same half revolution of the gantry, the index for the detectors $D_{2,k}$ is supplemented by the index number k with the values 0 and 1. The entire virtual detector 23 is thus formed from data from the narrow detector $D_1$ for the small section field 13 from one half revolution, and data from the large detector $D_2$ for the large section field 14 from two adjacent half revolutions 0 and 1.

Figure 3:
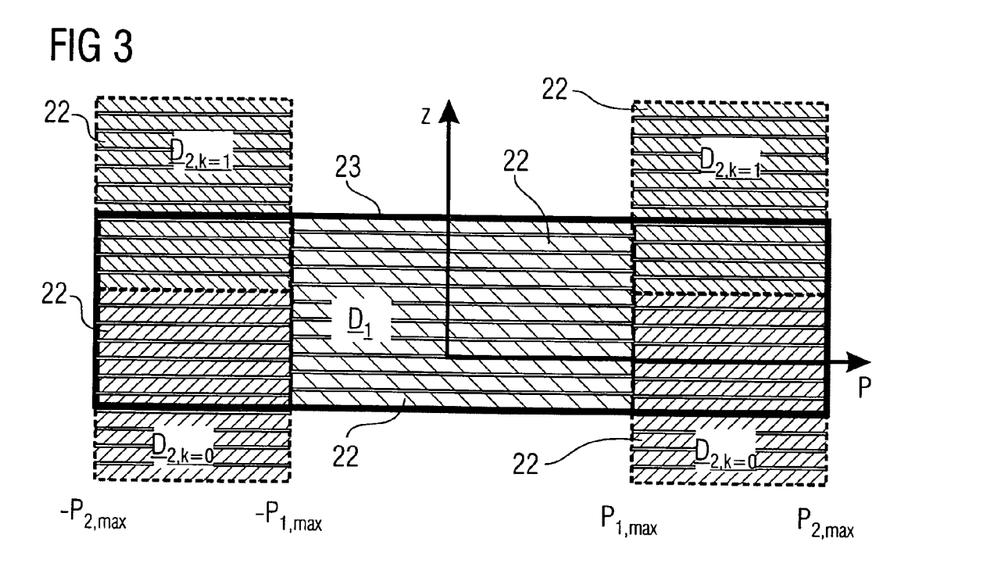
FIG. 3 shows the principle of supplementing data over two detectors.

If the two beams are set to be the same, then supplementing by the second focus detector combination is not possible in the area beyond the smaller section field 13. The length of the second detector $L_2$ is also designed to correspond to the maximum widening which can be set for the fan angle $\beta_2$, with only a central part of the detector being active, if required.

In an arrangement such as this of two focus detector combinations, CT images with twice the time resolution can be calculated from the data measured at the same time in the two detectors. This advantage is particularly important for coronary imaging since this allows the time resolution of an "electron beam tomography" (EBT) of 100 ms to be achieved with so-called 3rd generation CT scanners with a gantry rotation period of about 400 ms, as is currently available.

The basic principle of the SMPR method and of the fundamentally similar ACMPR method will be described first of all in the following text. This method breaks down the path from measured value recording to image calculation into four sections: data rebinning, calculation of intermediate images by filtering of projections and back-projection, reformatting of segment stacks to form segment images, and subsequent addition of the segment images.

In the SMPR/ACMPR method, incomplete intermediate images are first of all produced on double-inclined planes matched to the spiral. For this purpose, the spiral $SB_n$ is divided into sub-segments $USB_n$, each of which covers an angle of considerably less than 180°.

Figure 4:
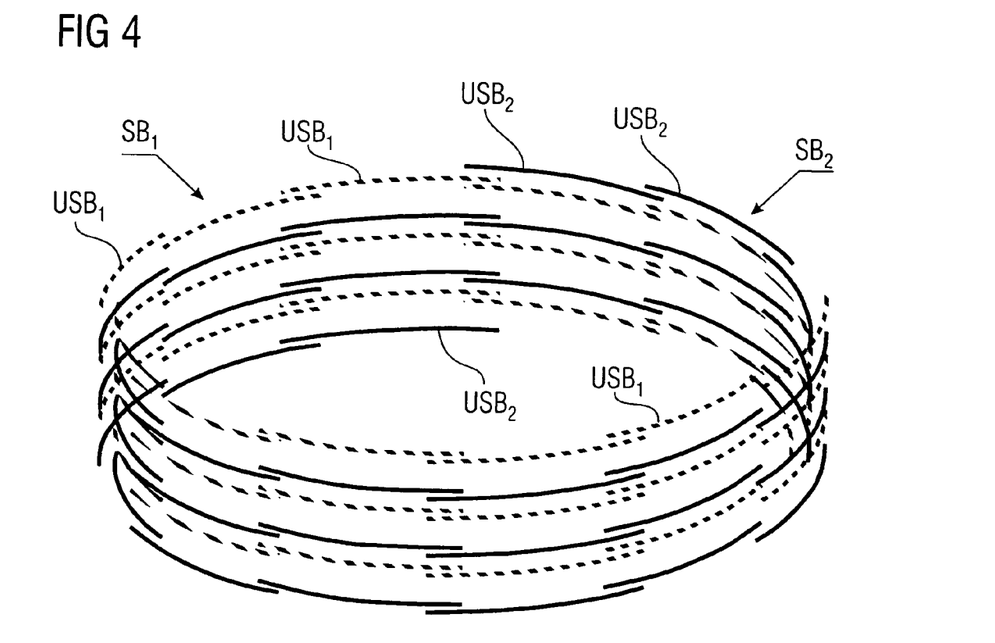
FIG. 4 shows a schematic illustration of the sub-sectors, which are arranged in a spiral shape, of a spiral of two focus detector combinations.

FIG. 4 shows the profile of the two spirals $SB_1$—solid lines—and $SB_2$—dashed lines—of the foci $F_1$ and $F_2$. This double spiral $SB_1$, $SB_2$ is furthermore divided into individual sub-segments $USB_n$, with each sub-segment covering approximately 30° in this case.

Figure 5:
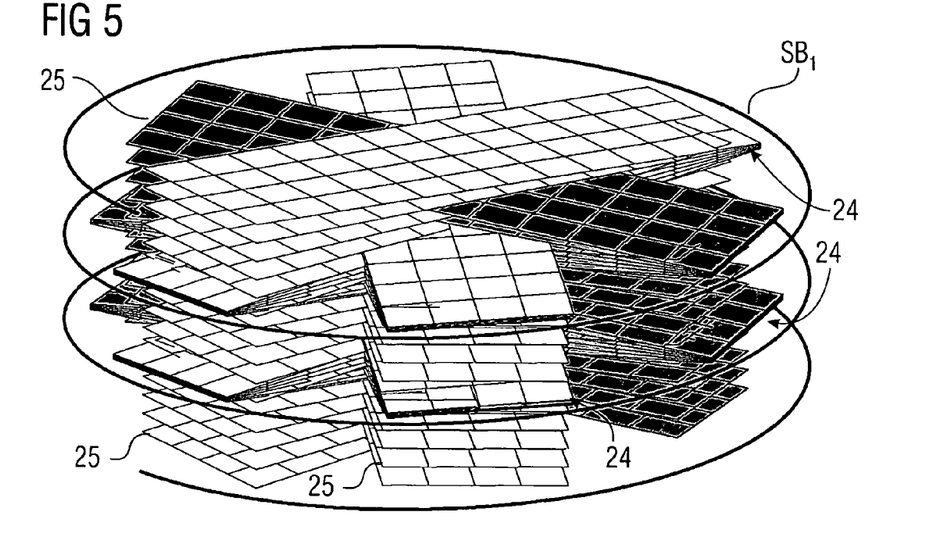
FIG. 5 shows segment image stacks, arranged in the form of a fan, for the spiral path of a single focus detector combination over a number of revolutions.

A large number of double-inclined segment image planes are produced from each individual sub-segment $USB_n$, corresponding to the number of lines in the detector that is used. By way of example, FIG. 5 shows such segment image stacks 24, which have a fan-shaped appearance, for a number of revolutions for the spiral path of a single focus detector combination. However, in order to assist clarity, the illustration shows a segment image stack 24 with the intermediate images 25 only for every alternate sub-segment.

Each sub-segment $USB_n$ thus results in segment image stacks 24 with a large number of intermediate images 25, which intersect on the spiral. If so many intermediate images 25 from one reference plane are now combined so as to result in a 180° data record from their sub-segments $USB_n$, then this results in a complete CT image. Since the image planes of each segment image stack are double-inclined in this case, reformatting is also required. Furthermore, it is also necessary to take account of the fact that the segment image stacks do not originate just from a single spiral, but from a number of spirals, in this case from the two spiral paths $SB_1$ and $SB_2$ in the example.

Figure 6:
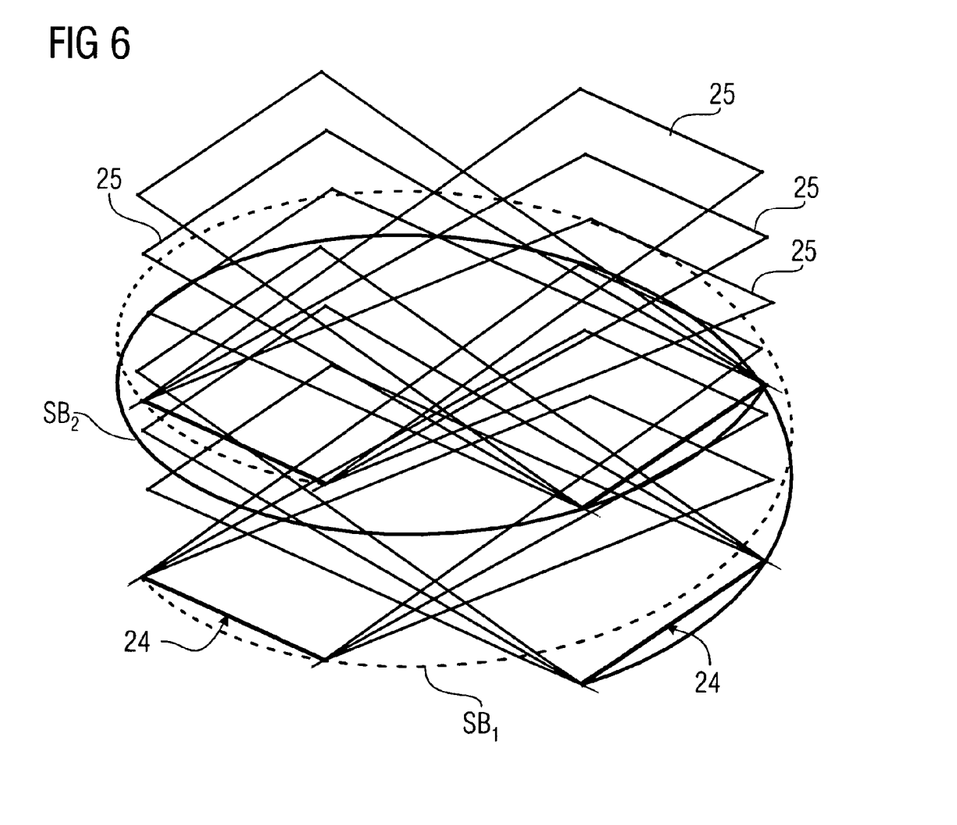
FIG. 6 shows segment image stacks, arranged in the form of a fan, for the spiral path of two focus detector combinations, offset through 90°, over two revolutions.

This situation is illustrated in FIG. 6, which shows the two spiral paths $SB_1$ and $SB_2$ and in each case two segment image stacks 24 for each spiral path, with the associated intermediate images 25. For clarity reasons, only three intermediate images 25 are shown in this illustration.

Figure 7:
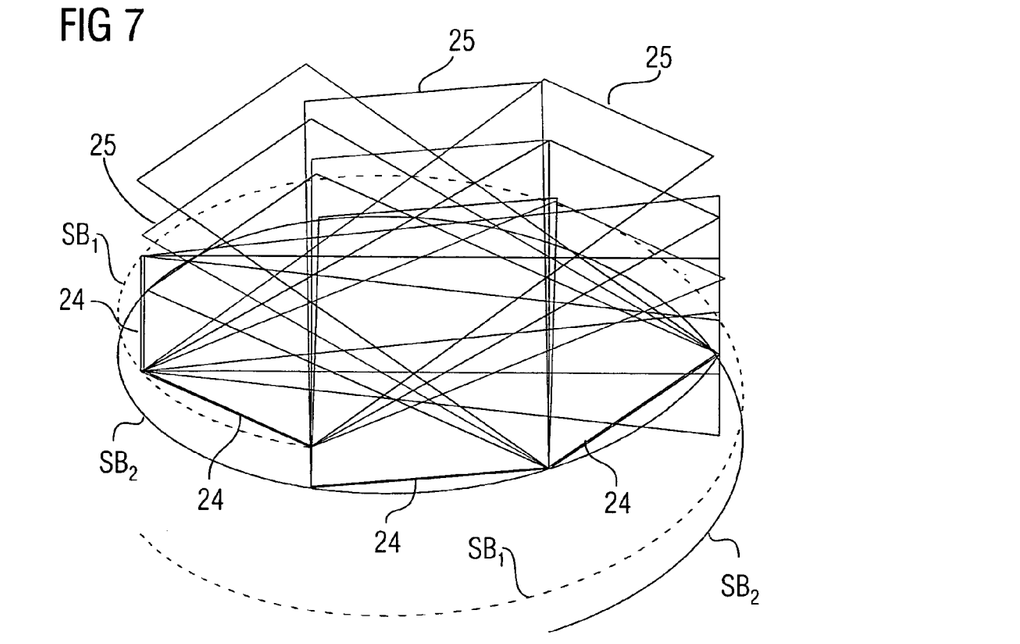
FIG. 7 shows segment image stacks, arranged in the form of a fan, for a complete 180° data record with the segment image stacks from two focus detector combinations, in each case for a 90° revolution.

Finally, FIG. 7 also shows a—likewise highly simplified and schematic—illustration of a complete 180° data record with the segment image stacks 24 and the associated intermediate images 25 from the two spiral paths $SB_1$ and $SB_2$, although this reaches the limit of what could be illustrated easily.

Since the intermediate images 25 of a segment stack 24 in the measurement volume considered here are not necessarily orthogonal with respect to the z axis of the scanner, they must be reformatted. During this reformatting process, the pixels in the intermediate images are interpolated on a transverse virtual plane, resulting in segment images relating to a specific z position. The z position of the virtual section plane can in principle be chosen freely. The weighting of the individual pixels in the numerous intermediate images, which are inclined in space, is carried out by means of a distance weighting function in the z direction, for which purpose a weighting with a triangular function has been found to be adequate. The reformatting step is carried out for a specific spiral angle segment and for its opposite segment, so that this results in a planar segment image on the virtual section plane.

So far, the spirals associated with the two focus detector combinations have been dealt with separately, that is to say reformatted separately. The segments, which each complement one another to form an angle of 90°, are taken from the two spirals $S_1$ and $S_2$ only in the following addition step. These must then be added to one another in a complementary form to cover an angle of 180°. In this final step, the individual segment images are now added up in order to produce a section image which can be utilized for diagnostic purposes. The use of two 90° spiral data records from two focus detector combinations which are arranged offset through 90° then results in twice the time resolution of a single focus detector combination, which would require twice the time to scan a 180° sector in its entirety.

Based on the method according to an embodiment of the invention, double-inclined segment images (=image layers) from a number of spiral paths with different foci are now reconstructed over a number of heart cycles for a heart phase which can be selected, although each of these is incomplete in its own right. The length of the reconstruction segments is determined in a multiple segment reconstruction process, corresponding to the local heart rate and the gantry rotation time. For image construction, it is necessary to use segment elements of the spiral data from adjacent heart cycles in the correct phase, which supplement one another for each spiral to form $\pi/2$, and to form $\pi$ with the data from the two spirals. After the reconstruction of the segment image stacks (=booklets) which are associated with each segment, these are reformatted to form axial segment image stacks (=axial booklets) and can be added layer by layer to form complete CT images with a segment length of $\pi(=180°)$.

While FIGS. 3 to 7, which have been mentioned so far, illustrate only the spatial situation of the two spiral paths of the foci used and their effect on data acquisition, the time component of the method according to an embodiment of the invention will now be described in FIGS. 8 and 9.

Figure 8:
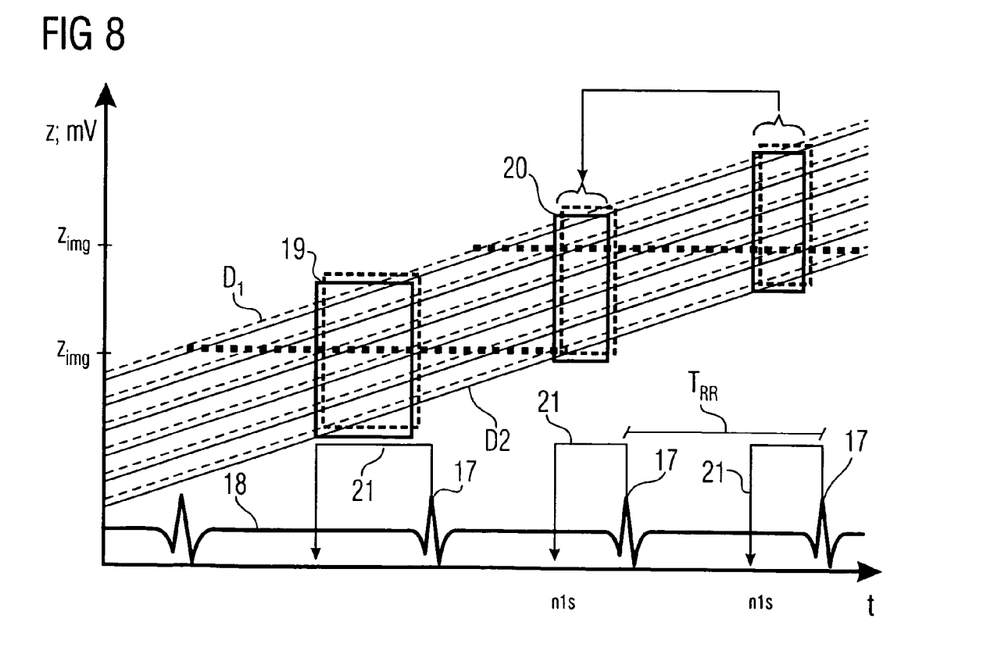
FIG. 8 shows the position profile of two 6-line detectors in the z direction as a function of the rotation angle of the gantry with an EKG signal measured in parallel in order to compare a 1-sector and a 2-sector reconstruction of an image position.

FIG. 8 shows schematically, the profile of the two detectors $D_1$ and $D_2$ over the z axis in relation to the rotation angle α, which is linearly coupled to the time axis t, owing to the constant spiral profile. The R spikes 17 are shown, plotted against the time, at the bottom of the figure, and related directly to the profile of the EKG line 18—mV/t coordinate. Working back from the position of the R spike, represented by the reference symbol 21, the start of the rest phase in each heart cycle is determined. The spiral data records $S_1$ and $S_2$ as recorded in the spiral mode with the two detectors $D_1$ and $D_2$ from this time in the cycle are used for display purposes. The lines which run obliquely from the bottom left of the figure represent the path of the detector lines along the z axis, with the dashed lines representing the profile of the detector lines of the detector $D_1$, and the solid lines representing the profile of the detector lines of the detector $D_2$.

With regard to the first reconstructable volume element of the heart, the figure in this case shows a reconstruction from data 19 for a single heart cycle, while data 20 from two successive heart cycles is used for the subsequent reconstruction, and these data items are joined together for an image position $z_{img}$. Segment image stacks from a number of successive heart cycles, preferably two successive heart cycles, are thus in each case calculated separately for the multiple sector reconstruction process according to an embodiment of the invention, and the intermediate images which result from this, and/or the segment images calculated from them, from different heart cycles but with the same heart phase are then added up, with the sum of the sub-segments used for this purpose adding up to π. This results in the desired better time resolution and thus in a sharper display of the heart and, in particular, of the coronaries. This can be seen in the illustration by the reduced time extent of the data gathered, as identified by the reference symbol 20.

When gathering image layers in the segment image stacks, care should also be taken to ensure on the one hand that the gantry is moved with a specific rotation period and, on the other hand, that the heart also changes between the movement phase and the rest phase at a frequency which may vary. If the aim is to achieve sharp CT images, then it is necessary to determine the images from as short a period of the rest phase as possible, in which case the gathering of complete data records covering π will not necessarily be trivial, owing to the two frequencies which occur.

These data records must on the one hand be in phase with the heartbeat and on the other hand must be at the correct angle with respect to the angular position of the number of foci being considered. FIG. 8 shows how the data records are gathered with the correct phase with respect to the heart frequency from two heart cycles. FIG. 9 now illustrates how spiral data records for the correct angle are gathered, in which case it is also necessary to take account of the angle offset of the two foci.

The selected data segments are at the correct angle when, on the one hand, the segment elements add up to form π/2 and, on the other hand, when the spiral data of $S_1$ and $S_2$ is offset to a rotational angle π/2 with respect to any given heart phase. The time resolution in the target image stack results from the maximum length of the segment elements used for reconstruction. The second sector $\theta_2$, which in each case adds up to form π/2, with its second spiral data record $S_2$ should now be selected corresponding to the ratio of four times the distance between two R spikes in the EKG to form one complete revolution of the gantry $4T_{RR}/T_{rot}$—starting with a first spiral data record $S_1$, which corresponds to a first sector $\theta_1$ which starts at the angle $\alpha_{n1s}$. By way of example, FIG. 9 shows a first sector $\theta_1$ which, in principle, can have added to it any of the other desired illustrated sectors $\theta_2$ to form a total sector covering π/2, with these being not only the two directly adjacent sectors but also their complementary sectors offset through π, which contain the same information. The illustrated first sector $\theta_1$ may thus have four other complementary sectors $\theta_2$ added to it. The actual position of the second sector $\theta_2$ to be used in this case depends on the ratio $4T_{RR}/T_{rot}$.

According to an embodiment of the invention, data from adjacent heart cycles is used for image construction, in order to achieve better time resolution than the known single-sector reconstruction process in the two-sector reconstruction process described here, thus resulting in a 180° data record, in each case comprising two sectors, each having two sub-segments. The two sub-segments of length $\Delta\theta_1$, $\Delta\theta_2 = \pi/2 - \Delta\theta_1$ have the start and end projections $\alpha_{n1s}, \alpha_{n1e}$ as well as $\alpha_{n2s}$ and $\alpha_{n1e}$ which, with respect to the time axis, correspond to the time positions $t_{n1s}, t_{n1e}$ as well as $t_{n2s}$ and $t_{n2e}$, respectively. The requirement for correct-angle segment elements means that:

$$\alpha_{2ns} = \alpha_{1ns} + \Delta\theta_1 + n_1 \cdot \pi/2$$

where $n_1$ is a natural number which has not yet been determined.

The projections must, furthermore, have the correct phase, that is to say $t_{n1s}$ and $t_{n2s}$ must be separated by the same time interval from the corresponding R peaks in the EKG. For example: $t_{n1s} = T_R(n+1) - T_{rev}$ and $t_{n2s} = T_R(n+2) - T_{rev}$; where $T_{rev}$ denotes the time offset before the next R peak. The same time interval means that:

$$\alpha_{2ns} = \alpha_{1ns} + 2\pi \frac{T_{RR}(n+1)}{T_{rot}} - n_1 \cdot \pi/2$$

where $T_{RR}(n+1) = T_R(n+2) - T_R(n+1)$ denotes the current heart cycle length and $T_{rot}$ denotes the rotation time of the gantry. After simple conversion operations, this results in:

$$\Delta\theta_1 = \left(\frac{4T_{RR}}{T_{rot}} - n_1\right) \cdot \pi/2 \text{ where } n_1 = \left\lfloor \frac{4T_{RR}}{T_{rot}} \right\rfloor;$$

Figure 9:
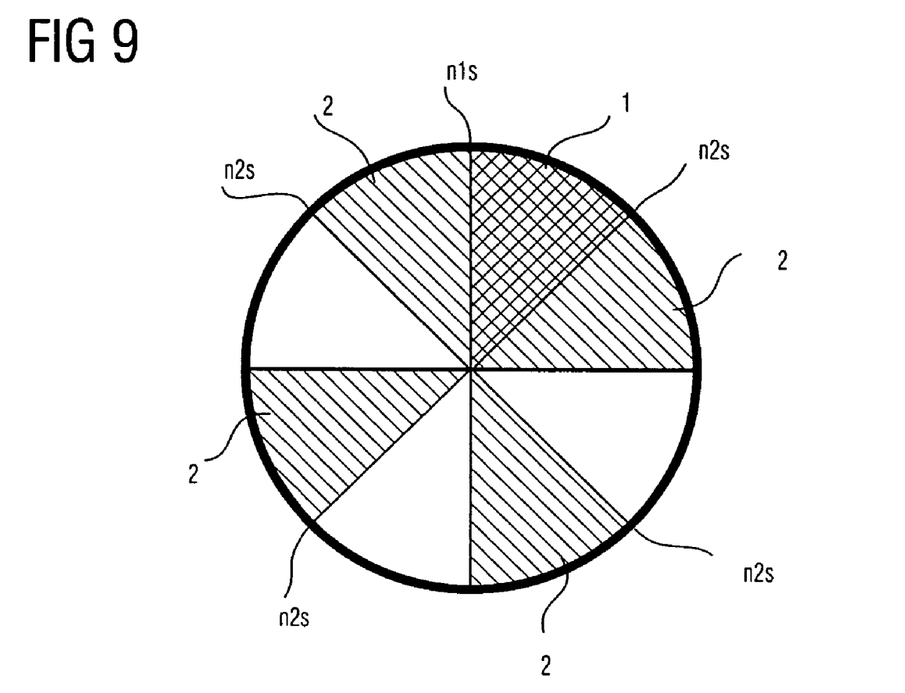
FIG. 9 shows the principle of sector selection for a 2-sector reconstruction.

The four possible cases of complementary supplementing of $\Delta\theta_1$ and $\Delta\theta_2$ shown in FIG. 9 result as a function of the instantaneous heart frequency and the gantry rotation time $T_{rot}$.

Overall, this therefore results in the following reconstruction pipeline:

1. Optional line by line parallel rebinning;
2. Line by line continuation of $D_1$ in the channel direction with data from $D_2$;
3. Separate ACMPR reconstruction of the spiral data records $S_1$ and $S_2$;

4. Layer by layer addition of the corresponding reformatted target volumes from the spiral $S_1$ and $S_2$ to form complementary π data records.

Since the spiral data records $S_1$ and $S_2$ are acquired at the same time, the segment elements $P_1$ and $P_2$ in a known single-sector reconstruction process have an associated time resolution $\Delta T_{ima} = T_{rot}/4$. With the currently possible gantry rotation time of about 400 ms, this results in a time resolution of about 100 ms, which is comparable to EBT, even in a single-sector reconstruction process. In the case of the two-sector reconstruction process according to the invention, the time resolution is dependent on the heart rate, and is defined by:

$$\Delta T_{ima} = \frac{\max(\Delta\theta_1, \Delta\theta_2)}{2\pi} \cdot T_{rot}.$$

In a good situation, this therefore results in $\Delta T_{ima} = T_{rot}/8$, while, in a poor situation, $\Delta\theta_1 = \pi/2$ results in the time resolution becoming $\Delta T_{ima} = T_{rot}/4$.

However, as a result of poor relationships between the gantry rotation period and the current heart frequency, it is also possible for a situation to arise in which it is not possible to gather complete data records covering π in the rest phase. In this situation, the inventors propose that adaptive changes be carried out between a single-sector reconstruction process and a two-section reconstruction process, depending on which makes it possible to achieve more complete data acquisition from the rest phase of the heart.

One particular embodiment of the method is therefore intended to make it possible to carry out the time sorting process adaptively. Owing to the currently available gantry rotation times, this means that—possibly during a scanning process—the single-sector reconstruction process should be used for lower heart rates and that the two-sector reconstruction process should be used for higher heart rates. This is then also dependent on switching between the two evaluation methods during the measurement.

It is self-evident that the features of the embodiments of the invention mentioned above can be used not only in the respectively stated combination but also in other combinations or on their own without departing from the scope of the invention.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for production of tomographic section images of a periodically moving object with periodically changing movement and rest phases, the method comprising:
    moving n focus detector combinations with flat detectors, to scan the at least partially periodically moving object, on n coaxial spiral paths relative to the object to be examined;
    gathering detector output data together from the detectors, which represent attenuation of beams which originate from foci as they pass through the examination object, the data being gathered together with at least one of the indirect and direct spatial orientation data of the beams;
    measuring movement signals of the moving object to detect movement and rest phases;
    storing time correlation between the movement data and the detector output data being stored;
    reconstructing axial segment image stacks, independently of one another, from sub-segments of the spiral paths using the detector output data from each detector representing a rest phase of the moving object, wherein segment image stacks from the n spiral paths of the n focus detector combinations at the correct time are added up in a complementary angle form and in layers to form 180° tomography section images, with the axial segment image stacks being reconstructed in a first step from double-inclined reconstruction planes and, in a second step, being reformatted to produce axial segment image stacks, and wherein detector data from a number of successive movement periods are used.

2. The method as claimed in claim 1, wherein data from simultaneous 180°/n rotations of the n focus detector combinations is used for a complete 180° image stack.

3. The method as claimed in claim 1, wherein a parallel rebinning process is carried out before back-projections are carried out.

4. The method as claimed in the preceding patent claim 3, wherein the parallel rebinning process is carried out line by line.

5. The method as claimed in claim 1, wherein only two focus detector combinations are used, whose angles are offset with respect to one another and which are arranged at right angles to one another.

6. The method as claimed in claim 1, wherein only three focus detector combinations are used, whose angles are offset with respect to one another.

7. The method as claimed in claim 1, wherein at least one focus detector combination is used, whose aperture angle is greater than the aperture angle of the at least one other focus detector combination.

8. The method as claimed in claim 1, wherein each focus detector combination runs on a dedicated spiral path which is offset with respect to the spiral paths of the other focus detector combinations.

9. The method as claimed in claim 1, wherein at least two focus detector combinations are arranged offset with respect to one another in the z direction such that they run on a common coincident spiral path.

10. The method as claimed in claim 9, wherein the offset of the at least two focus detector combinations in the z direction is set as a function of a selected gradient of the spiral path.

11. The method as claimed in claim 1, wherein the rotation time of the focus detector combinations is set such that this results in the best-possible time resolution in a multiple segment reconstruction.

12. The method as claimed in claim 1, wherein, in order to reduce a dose load on the examination object, radiation which originates from at least one focus is controlled at least one of indirectly and directly by the measured movement signals being switched off over at least the majority of the movement phase.

13. The method as claimed in claim 7, wherein the data from the focus detector combination with a small fan angle, which covers a relatively small section field, is used by data from the focus detector combination with a large fan angle, which covers a larger section field, to supplement the detector data from the larger detector.

14. An imaging CT scanner, comprising:
two coaxially arranged focus detector combinations, movable in a spiral shape along a common rotation axis in order to scan a periodically moving object;
means for detecting movement and for distinguishing between rest and movement phases of the periodically moving object;
means for performing the method of claim 1.

15. The CT scanner as claimed in claim 14, wherein at least two focus detector combinations use fan aperture angles of different size.

16. The CT scanner as claimed in claim 15, wherein the magnitude of the fan aperture angle is adjustable on at least one focus detector combination.

17. The CT scanner as claimed in claim 14, wherein the distance between the focus and the detector is different for two focus detector combinations.

18. The method of claim 1, wherein the method is for production of X-ray CT images of a periodically moving object with periodically changing movement and rest phases, the attenuated beams being attenuated X-ray beams.

19. The method of claim 18, wherein the object is a heart of a living being.

20. The method as claimed in claim 2, wherein a parallel rebinning process is carried out before back-projections are carried out.

21. The method as claimed in claim 6, wherein the angles are offset through 180°/3.

22. The imaging scanner as claimed in claim 14, wherein the imaging CT scanner is an X-ray CT scanner, wherein the attenuated beams are attenuated X-ray beams.

23. The CT scanner as claimed in claim 15, wherein the distance between the focus and the detector is different for two focus detector combinations.

24. The CT scanner as claimed in claim 16, wherein the distance between the focus and the detector is different for two focus detector combinations.

25. An apparatus for production of tomographic section images of a periodically moving object with periodically changing movement and rest phases, the apparatus comprising:
means for moving n focus detector combinations with flat detectors, to scan the at least partially periodically moving object, on n coaxial spiral paths relative to the object to be examined;
means for gathering detector output data together from the detectors, which represent attenuation of beams which originate from foci as they pass through the examination object, the data being gathered together with at least one of the indirect and direct spatial orientation data of the beams;
means for measuring movement signals of the moving object to detect movement and rest phases;
means for storing time correlation between the movement data and the detector output data being stored; and
means for reconstructing axial segment image stacks, independently of one another, from sub-segments of the spiral paths using the detector output data from each detector representing a rest phase of the moving object, wherein segment image stacks from the n spiral paths of the n focus detector combinations at the correct time are added up in a complementary angle form and in layers to form 180° tomography section images, with the axial segment image stacks being reconstructed first from double-inclined reconstruction planes and, next being reformatted to produce axial segment image stacks, and wherein detector data from a number of successive movement periods are used.

* * * * *